United States Patent [19]

Craig

[11] Patent Number: Plant 6,247

[45] Date of Patent: Aug. 16, 1988

[54] GERANIUM PLANT "HELEN"

[75] Inventor: Richard Craig, State College, Pa.

[73] Assignee: Research Corporation, N.Y.

[21] Appl. No.: 882,129

[22] Filed: Jul. 3, 1986

[51] Int. Cl.[4] ..... A01H 5/00
[52] U.S. Cl. ..... Plt./68
[58] Field of Search ..... Plt. 68

*Primary Examiner*—Robert E. Bagwill

*Attorney, Agent, or Firm*—Scully, Scott, Murphy & Presser

[57] ABSTRACT

This invention relates to a new distinct cultivar of geranium, substantially as illustrated and described, characterized as being particularly well adapted to both commercial greenhouse production and garden performance, possessing unique flavonol and anthocyanin profiles and having more fully double flowers, better garden performance, and better heat tolerance when compared with geranium cultivar "Ivalo".

3 Drawing Sheets

The present invention relates to a new and distinct cultivar of geranium *Pelargonium*×*hortorum* called "Helen". The cultivar is particularly well adapted to both commercial greenhouse production and garden performance. The cultivar's novel characteristics include more fully double flowers, better garden performance and better heat tolerance when compared with "Ivalo". The cultivar is further characterized by unique biochemical fingerprint profiles.

The cultivar was developed from an organized, scientifically designed breeding program carried out at the Department of Horticulture, The Pennsylvania State University, University Park, Pa. 16802 and specifically resulted from selection in the progeny of a cross between geranium cultivars "Bruni"×"Ivalo". The selection was asexually propagated by cuttings and the reproductions ran true.

With reference to the detailed description of the cultivar which follows, the test plant was grown in full sun under glass, 62° F. night and 68° F. cloudy days, 75° F. sunny days. Soilless medium was fertilized once per week with 15-15-15 at 275 ppm N. Color readings were taken under cool white fluorescent lamps at 150 foot-candles and color identification was by reference to the Royal Horticultural Society Colour Charts except where common terms of color definition are employed.

| Peak No. |
|---|
| 1. Delphinidin 3,5-diglucoside |
| 2. Cyanidin 3,5-diglucoside |
| 3. Pelargonidin 3,5-diglucoside |
| 4. Peonidin 3,5-diglucoside |
| 5. Malvidin 3,5-diglucoside |

Figure 3:
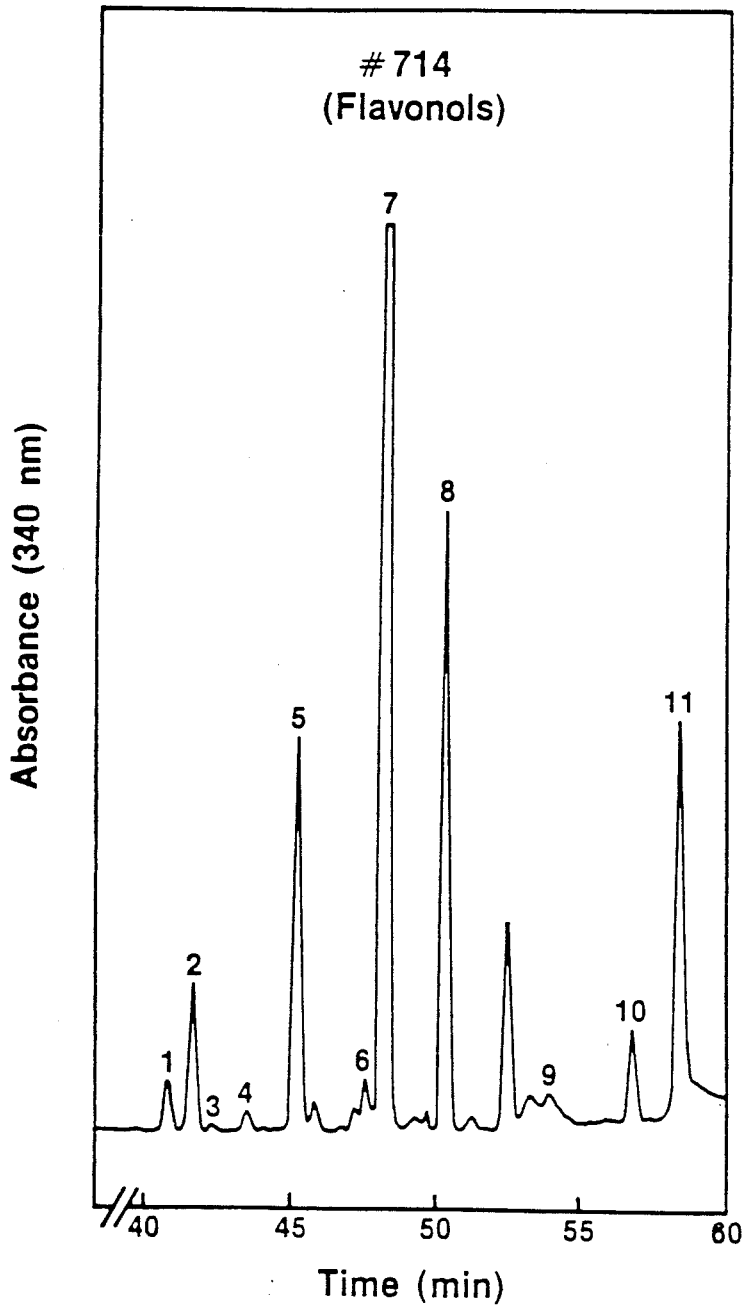

FIG. 3 illustrates the flavonol profile obtained from HPLC. Quantitative values are found in the tables.

| Peak No. |
|---|
| 1. Quercetin 3-rhamnosylgalactoside |
| 2. Quercetin 3-rutinoside |
| 3. Quercetin 3-galactoside |
| 4. Quercetin 3-glucoside |
| 5. Kaempferol 3-rhamnosylgalactoside |
| 6. Kaempferol 3-galactoside |
| 7. Kaempferol 3-rutinoside |
| 8. Kaempferol 3-glucoside; Kaempferol 7-glucoside; Quercetin 3-rhamnoside |
| 9. Kaempferol 3-xyloside |
| 10. Kaempferol 3-arabinoside |
| 11. Kaempferol 3-rhamnoside |

THE PLANT

Classification:

*Botanical.*—*Pelargonium*×*hortorum.*

*Tradename.*—#714 (80-220-1)="Helen".

Form: Compact, globe.

Height: 21.0–25.0 cm.

Growth: Short internodes, self branching; medium-size stem (diameter); flowers borne close to foliage.

Leaves:

*Size.*—6.0–9.0 cm across.

*Shape.*—Reniform, variously lobed.

*Margin.*—Crenate.

*Texture.*—Pubescent.

*Color.*—Fan 3, green group, 137-C (RHSCC) Top; 138-B (RHSCC) Bottom.

*Ribs and veins.*—Palmate veins. Ribs suppressed and distinct. Fan 3, yellow-green group 144-D (RHSCC).

Petioles: Stalked 5.0–7.0 cm long, medium caliper.

Stem: Medium caliper.

*Color.*—Fan 3, green group 143-C (RHSCC).

Internodes: 1.5–2.0 cm.

THE BUD

Shape: Initially ovate.

Size: 1.5 cm diameter.

INFLORESCENCE

Blooming habit: Smaller bloom but more floriferous than typical geranium; flat top; flowers borne close to foliage.

Size: 8.0–12.0 cm across.

Borne: Heavy, strong peduncle; modified umbel.

Florets:

*Form.*—Round, irregular; cupped; 3.5–4.5 cm; semi-double; overall clear pink with ruby-red blotch on petals.

*Petals.*—11–14.

*Size.*—2.0–2.5 cm long and 1.0–2.0 cm wide.

*Texture and appearance.*—Smooth; dull color. Base: Pure white to red-purple, Fan 2, red-purple group 62-B (RHSCC). Mid-veins and blotch: Fan 2, red-purple group 57-A (RHSCC). Top: Fan 2, red-purple group 61-D (RHSCC). Reverse: Fan 2, red-purple group 62-B (RHSCC).

Petaloids:

*Quantity.*—4–6.

*Shape.*—1.5–2.5 cm long; narrow and twisted.

*Color.*—Same as petals.

Pedicel: 2.5–3.0 cm in length.

Peduncle: 11.0–16.0 cm long; strong.

Persistence: Non-shattering; will hold 3–4 weeks.

Disease resistance: Not evaluated.

Lasting quality: Excellent, 3 weeks or longer.

REPRODUCTIVE ORGANS

Stamens: 3–4.

*Anthers.*—Small, brown 2.0–3.0 mm.

*Filaments.*—Flat white, 1.0 cm long; tips tinted rose-purple; small twisted petaloids attached.

*Pollen.*—Straw-colored (mature).

Pistils:

*Number.*—1.

*Length.*—0.75–1.0 cm.

*Stigma.*—5- or 6-lobed; rose-colored.

*Style.*—Green; 0.5 cm.

Ovaries: Green; globe-shaped; 5- or 6-lobed; pubescent.

Fruit: None.

BIOCHEMICAL PROFILES

In recent years, biochemical analysis has played an increasing role in plant systematics and taxonomy. In order to further characterize the cultivar, flavonols and anthocyanins were extracted from florets of the cultivar and its parents and subjected to analysis by high pressure liquid chomatography (HPLC). Background information supporting the validity of the HPLC technique can be found in an article by Asen & Griesbach ("High Pressure Liquid Chromatographic Analysis of Flavonoids in Geranium Florets as an Adjunct for Cultivar Identification", S. Asen and R. Griesbach, *J. Amer. Soc. Hort. Sci.* 108(5):845–850 (1983)), the contents of which are incorporated herein by reference. Briefly, the method for performing the analysis was carried out as follows:

Flavonoid extraction. The sample size for flavonoid identification consisted of the petals from six florets just after anthesis. Three different samples were collected from each cultivar and handled separately for analysis. The petals were weighed, ground in 20 ml of 1% HCl-MeOH with a mortar and pestle, filtered through one layer of Whatman #1 filter paper, and washed with 1% HCl-MeOH. The volume was adjusted to 90 ml and 2–15 ml aliquots were removed for the analysis and handled separately. Each aliquot was taken to dryness at 40° C. in vacuo. All traces of HCl were removed by azeotropic distillation with MeOH. One of the dried extracts was reconstituted in 2 ml of 1% HCl-MeOH and was used for anthocyanin analysis. The other was reconstituted in 2 ml of MeOH and was used for flavonol analysis. Each sample was stored at −34° C. until analyzed.

HPLC. Samples were analyzed on a Waters High Performance Liquid Chromatograph equipped with an automatic injection system (Waters Assoc. Wisp 71OA), dual pumps (Waters Assoc. Model 6000A), solvent programmer (Waters Assoc. Model 600), data module (Waters Assoc.), variable wavelength detector (Waters Assoc. Model 480), and a $C_{18}$ column (25 cm×0.46 cm and 5 μm particle size, Supelco).

Most of the flavonol compounds were separated by a linear gradient of 8% to 23% pump B over 55 min (pump A=1% triethylamine buffered to pH 3.0 with $H_3PO_4$ (TEAP); pump B=$CH_3CN$) at a flow rate of 1.2 ml/min and a chart speed of 0.5 cm/min. Detection was at 340 nm.

The anthocyanins were resolved by a linear gradient of 30% to 50% pump B over 40 min (pump A=1.5% $H_3PO_4$; pump B=20% HOAc+25% $CH_3CN$+55% of 1.5% $H_3PO_4$) at a flow rate of 1.0 ml/min and a chart speed of 0.5 cm/min. Detection was at 546 nm utilizing a fixed wavelength detector.

The flavonoids were quantified by injecting standards and comparing their peak areas with those from the plant samples. The results are expressed as ug of flavonoid/g fresh weight of plant material.

RESULTS

Figure 1:
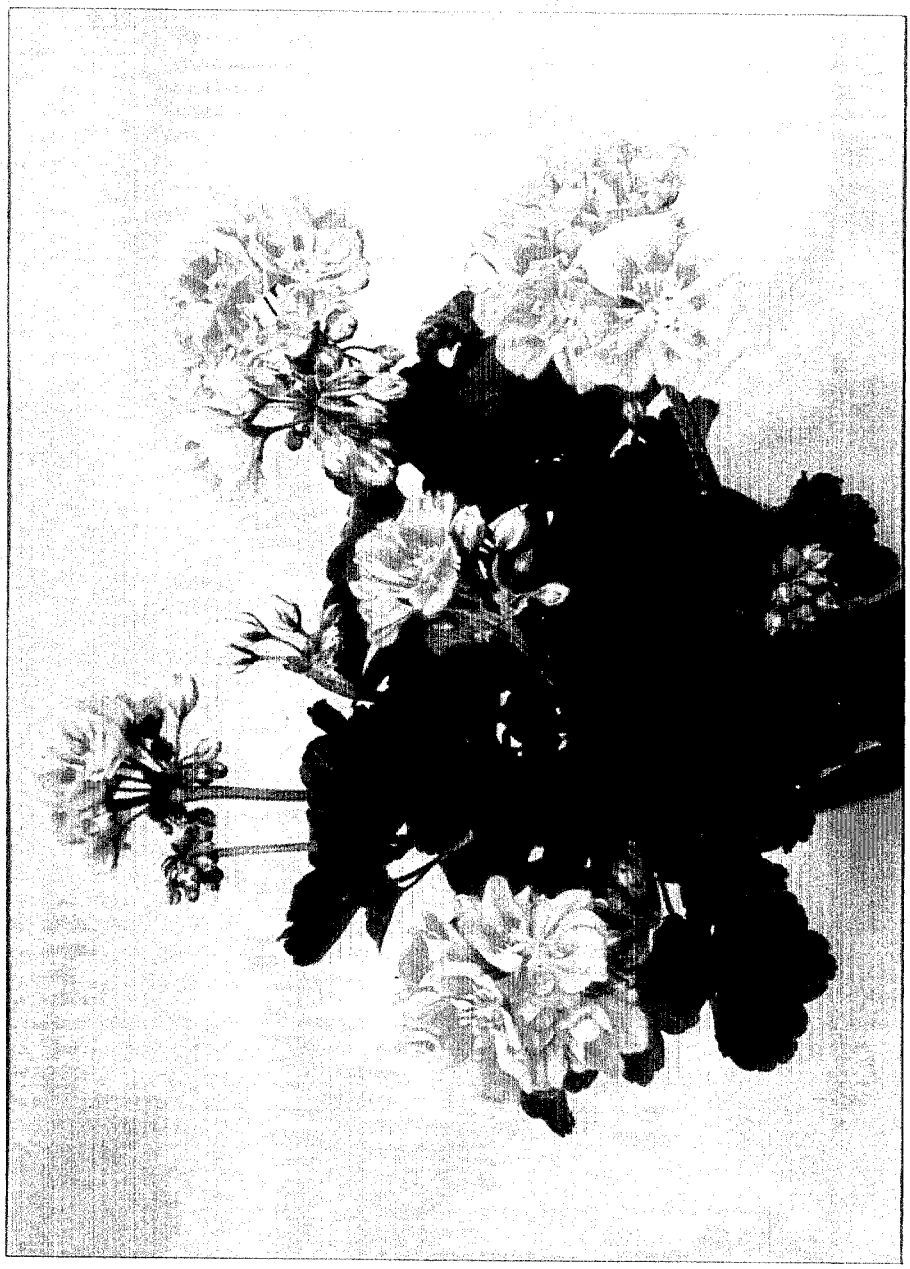
FIG. 1 illustrates in color the cultivar including foliage and flowers.
Figure 2:
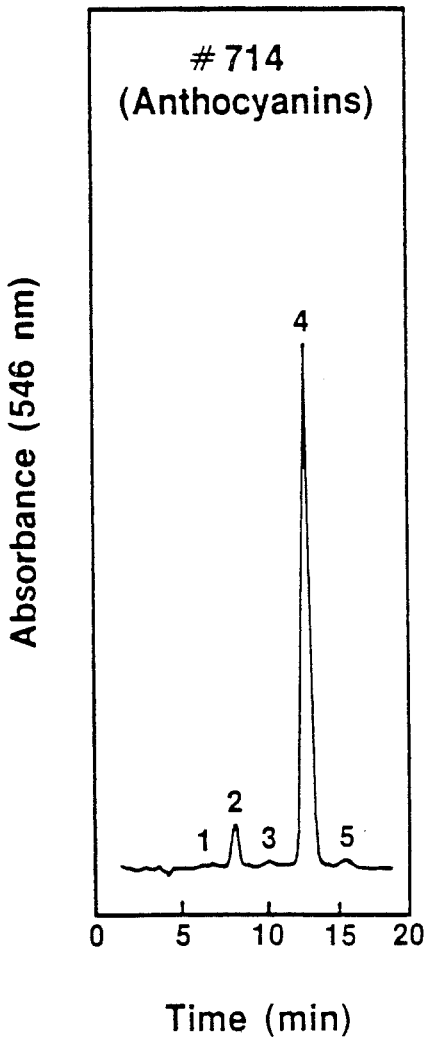
FIG. 2 illustrates the anthocyanin profile obtained from HPLC. Quantitative values are found in the tables. Analyses included a single peak that represented both pelargonidin and petunidin 3,5-diglucosides. Corrections were made in accompanying tables.

Chromatographic profiles for anthocyanins and flavonols are presented in FIGS. 2 and 3, respectively; quantification of these profiles by comparison to standards is presented in Tables 1 and 2, respectively.

The anthocyanins petunidin and pelargonidin 3,5-diglucoside were not resolved by the solvent system used. Past research has shown only negligible amounts of petunidin 3,5-diglucoside to be present in geranium florets compared to pelargonidin 3,5-diglucoside. In light of this, the peak corresponding to petunidin and pelargonidin 3,5-diglucoside was quantified as pelargonidin 3,5-diglucoside.

Kaempferol 3-rhamnoside could not be quantitated for several cultivars and is designated as ND (not determined). The chromatograms showed a small, wide peak in the region of elution for this compound. If a substantial amount of this compound were present, a distinct peak appeared but minute quantities, if present, were masked.

Barriers to quantitation of several flavonols existed. Kaempferol 3-glucoside, kaempferol 7-glucoside, and quercetin 3-rhamnoside all had the same retention time under these conditions. If these compounds are needed to distinguish between cultivars, they would have to be separated by other solvents or column types. Quercetin 3-xyloside appeared in several of the comparisons, but standards were not available to quantify this compound.

TABLE 1

| Anthocyanin concentration in petals of geranium florets | | | | | | |
|---|---|---|---|---|---|---|
| | μg anthocyanidin 3,5-diglucoside/g fresh wt. | | | | | |
| Cultivar | Delphinidin | Cyanidin | Pelargonidin | Peonidin | Malvidin | Total |
| 714 | —[z] | 23 | t[y] | 422 | t | 455 |
| Bruni | — | 78 | 5251 | 2418 | — | 7747 |
| Ivalo | t | 42 | t | 351 | t | 408 |

[z]— = not detected

[y]t = trace < 10 μg

TABLE 2

Flavonol concentration in petals of geranium florets

| | μg/g fresh wt. | | | | | |
|---|---|---|---|---|---|---|
| Cultivar | Qu3-[z] rhagal | Qu3-rut | Qu3-gal | Qu3-glu | Km3-rhagal | Km3-gal |
| 714 | 22 | 51 | t[y] | t | 189 | 11 |
| Bruni | 11 | 34 | —[w] | t | 307 | 47 |
| Ivalo | 11 | 32 | t | t | 132 | t |

| | μg/g fresh wt. | | | | |
|---|---|---|---|---|---|
| Cultivar | Km3-rut | Km3-xyl | Km3-arab | Km3-rha | Total |
| 714 | 617 | 21 | 22 | 126 | 1069 |
| Bruni | 1257 | 13 | 49 | 185 | 1908 |

TABLE 2-continued

Flavonol concentration in petals of geranium florets

| | | | | | |
|---|---|---|---|---|---|
| Ivalo | 470 | t | 10 | 114 | 789 |

[z]Abbreviations: Km = Kaempferol; Qu = Quercetin; arab = arabinoside; gal = galactoside; glu = glucoside; rha = rhamnoside; rhagal = rhamnosylgalactoside; rut = rutinoside; xyl = xyloside.
[y]t = trace < 10 μg.
[w]— = not detected.

What is claimed is:

1. A new distinct cultivar of geranium, substantially as illustrated and described, characterized as being particularly well adapted to both commercial greenhouse production and garden performance, possessing unique flavonol and anthocyanin profiles and having more fully double flowers, better garden performance, and better heat tolerance when compared with geranium cultivar "Ivalo".

* * * * *